United States Patent

Dukor

[11] Patent Number: 5,945,674
[45] Date of Patent: Aug. 31, 1999

[54] METHOD OF IDENTIFYING CELLULAR TYPES IN A BIOLOGICAL SAMPLE SUPPORTED ON AN ABSORPTIVE SUBSTRATE BY INFRARED SPECTROSCOPY

[75] Inventor: Rina K. Dukor, Elmhurst, Ill.

[73] Assignee: Vysis, Inc., Downers Grove, Ill.

[21] Appl. No.: 08/902,820

[22] Filed: Jul. 30, 1997

[51] Int. Cl.[6] ................................. G01N 21/35
[52] U.S. Cl. ................... 250/339.11; 250/341.8
[58] Field of Search ............ 250/339.11, 339.01, 250/341.8; 600/473

[56] References Cited

U.S. PATENT DOCUMENTS

| | | |
|---|---|---|
| 5,038,039 | 8/1991 | Wong et al. . |
| 5,072,382 | 12/1991 | Kamentsky ............... 250/360.1 |
| 5,168,162 | 12/1992 | Oong et al. . |
| 5,569,921 | 10/1996 | Sato et al. ............... 250/339.07 |
| 5,596,992 | 1/1997 | Haaland et al. ........... 250/339.11 |
| 5,818,046 | 10/1998 | Rizvi ........................ 250/339.12 |

FOREIGN PATENT DOCUMENTS

| | | |
|---|---|---|
| WO 91/11701 | 8/1991 | WIPO . |
| WO 96/00892 | 1/1996 | WIPO . |
| WO 96/41152 | 12/1996 | WIPO . |
| WO 96/41153 | 12/1996 | WIPO . |
| WO 97/30338 | 8/1997 | WIPO . |
| WO 97/30340 | 8/1997 | WIPO . |

OTHER PUBLICATIONS

"A Novel Reflective FT–IR Microscopy Method" by Denise Wade Rafferty and R. Craig Virnelson *Spectroscopy*, an Advanstar Publication—Jun. 1997, vol. 12, No. 5, pp. 42–44.

"Uniting Microscopy and Spectroscopy", by John A. Reffner and Pamela A. Martoglio *Practical Guide to Infrared Microspectroscopy—Practical Spectroscopy Series*, vol. 19–pp. 59–66, 1995.

"Multivariate Classification of the Infrared Spectra of Cell and Tissue Samples" by David M. Haaland, Howland D. T. Jones, and Edward V. Thomas—*Applied Spectroscopy*, vol. 51, No. 3, 1997, pp. 340–345.

*Primary Examiner*—Constantine Hannaher
*Attorney, Agent, or Firm*—Norval B. Galloway

[57] ABSTRACT

A method of detecting cellular types in a biological sample supported on an infrared absorptive substrate, such as a plain glass slide, analyzes infrared light reflected from the sample using an Attenuated Total Reflection (ATR) technique. An infrared beam is directed to the sample through an ATR microscope objective. The depth of penetration of the infrared beam in the sample is controlled to avoid infrared spectral response from the absorptive substrate. The attenuated total reflection from the sample is detected and analyzed to determine the cellular types or the presence of anomalies in the sample. The method allows infrared measurements on cell samples mounted on plain glass slides, as are normally used by pathologists and other medical investigators.

24 Claims, 2 Drawing Sheets

U.S. Patent　　　Aug. 31, 1999　　　Sheet 1 of 2　　　5,945,674
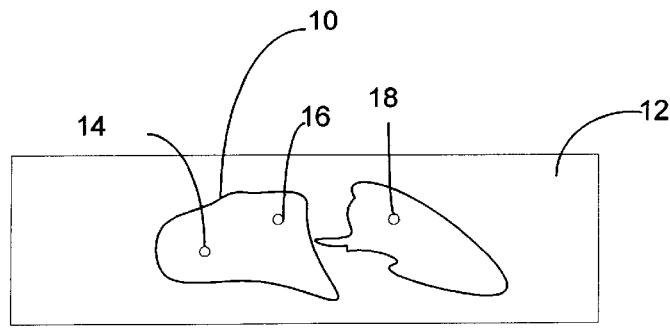
FIG. 1
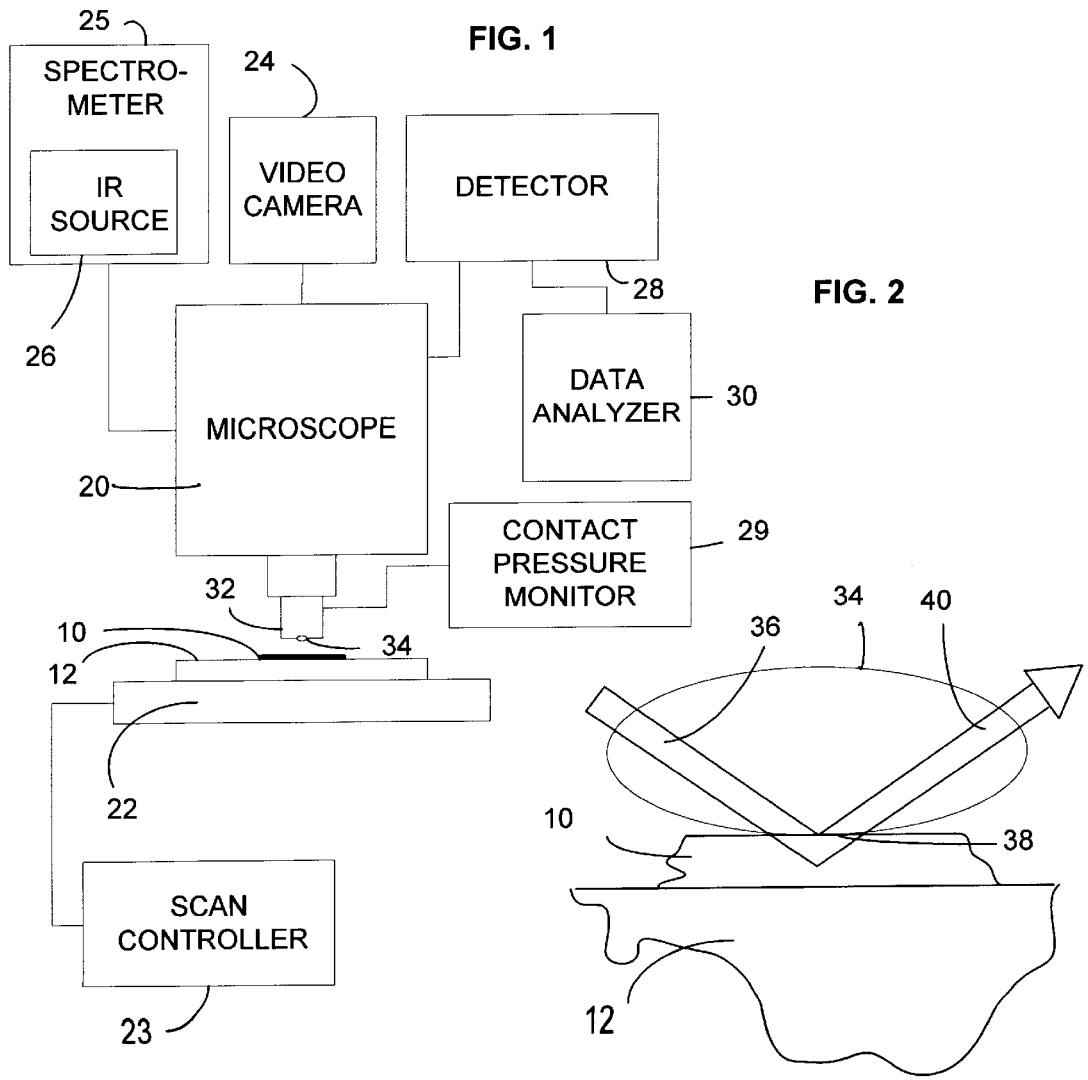
FIG. 2
FIG. 3

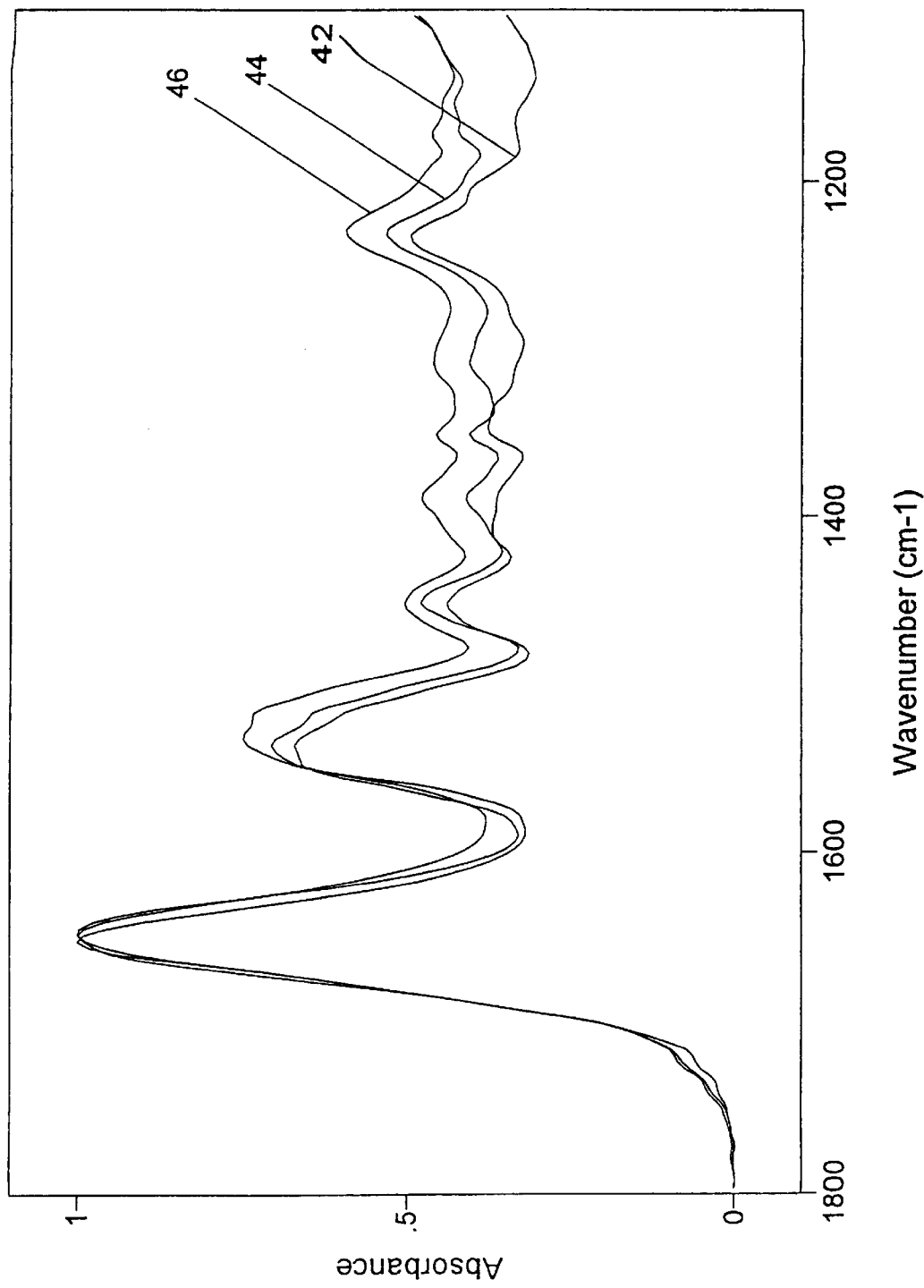

METHOD OF IDENTIFYING CELLULAR TYPES IN A BIOLOGICAL SAMPLE SUPPORTED ON AN ABSORPTIVE SUBSTRATE BY INFRARED SPECTROSCOPY

FIELD OF THE INVENTION

This invention relates generally to the examination of biological samples for identifying cellular types or the presence of cellular anomalies. More particularly the invention relates to the use of infrared spectroscopy to study biological samples for identifying cellular types or the presence of anomalies.

BACKGROUND OF THE INVENTION

In the past decade, applications of spectroscopy and microspectroscopy have greatly advanced into areas of clinical study. The potential of various spectroscopic techniques, including mid-infrared spectroscopy, for screening and disease diagnosis in clinical settings has been investigated. Research has been conducted on samples from a variety of organs and cellular types. The results of those studies have generally confirmed that infrared spectroscopy can differentiate malignant from normal cells.

As is well known, infrared spectroscopy is typically performed in either of transmission or reflection modes. The energy range of the infrared light used is typically in the mid-infrared range of about 4000 $cm^{-1}$ to 400 $cm^{-1}$. When operating in the transmission mode, the infrared beam passes through the sample once and is detected. When the energy incident to the sample matches an excitation energy of the sample material, energy is absorbed and the intensity of the incident radiation is reduced as a result. A detector measures the intensity of the transmitted light as a function of energy for identifying the energy absorbed. When operating in the reflection mode, the sample is placed on a reflective substrate such as a thin metal layer that does not absorb the incident infrared energy. The incident beam passes through the sample as for a transmission measurement but is then reflected off the substrate and passes through the sample a second time before it is detected. As for the transmission mode, energy from the incident beam is absorbed when the energy of the beam matches an excitation energy of the sample material and, as a result, the intensity of the incident light is reduced.

Samples for mid-infrared spectroscopy are conventionally prepared in a manner that is incompatible with that commonly used in a pathology laboratory. Typically, mid-infrared measurements are carried out on thin sections of microtomed tissue placed between two windows of infrared-transparent material, such as $BaF_2$ or $CaF_2$, or in a diamond anvil cell. Other studies involve the suspension of cells, centrifugation of cells into a pellet, extraction of DNA from tissues, or measurement of biological fluids in solution.

More recently, infrared microspectroscopy has been used in the study of such samples. This technique enables measurement of microscopic tissue areas and mapping of the whole tissue with the capability of visualizing the areas measured. Samples for infrared microspectroscopy are conventionally placed on an infrared-transparent material, such as $BaF_2$ or $CaF_2$ windows, for transmission measurements, or on gold-coated slides for reflection measurements. Gold provides a good reflective surface so that gold slides are the conventional choice for infrared reflection studies.

The results of the spectroscopic measurements are typically compared to the results of a study by a pathologist on a separate sample from the same source for classification. A pathologist uses visible microscopy to analyze a biological sample. The sample for pathologic study is conventionally a thin section fixed on a glass slide and stained. Glass slides, which are transparent to visible light, are inexpensive and easy to work with. In contrast, a gold coated slide typically costs several times more than a plain glass slide. Plain glass, however, is strongly absorptive in the mid-infrared range. Thus, when coupled with conventional infrared spectroscopic techniques, the glass absorption would be expected to overwhelm the spectral response from the sample in transmission measurements. A plain glass slide is also unsuitable for reflection measurements because it does not provide a good reflective surface. Significantly, samples prepared for standard pathologic studies are generally deemed unsuitable for infrared measurements due to the use of a plain glass slide as the supporting substrate.

Moreover, regardless of its exact method of preparation, a sample prepared in the conventional manner for infrared studies is damaged such that it cannot be recovered for examination by a pathologist to verify the diagnoses based on the infrared measurements or to perform any other pathologic study. At the same time, older samples mounted on glass slides and preserved for archival purposes cannot be subjects for analysis by conventional infrared spectroscopic techniques. The use of different samples prepared in different ways for spectroscopic and conventional pathologic studies also inevitably introduces some unreliability in the comparison of the results from the two different studies.

SUMMARY OF THE INVENTION

In view of the foregoing, it is a primary object of the invention to provide a method for identifying cellular types or the presence of anomalies in biological samples by infrared measurements that is non-destructive and requires no special sample preparation.

It is a related and more specific object of the invention to provide a method for identifying cellular types or the presence of anomalies in biological samples by infrared spectroscopy that can be applied to samples prepared for conventional pathologic studies.

In accordance with these and other objects of the invention, there is provided a method of identifying cellular types and/or anomalies in a biological sample supported on an infrared-absorptive substrate, such as a plain glass slide, by infrared spectroscopy. By cellular type is meant to include any of a number of states which are said to characterize cells such as benign, hyperplastic, and malignant, and different types of cells such as epithelial cells (found in lobules, ducts and elsewhere), endothelial cells (found in blood vessels and elsewhere), and fibroblasts (found in connective tissue and elsewhere), and others. Abnormal cells, such as cancerous cells, are considered anomalous and are identifiable by the method of the invention. Thus, the method of the invention is useful in cancer diagnostics and for monitoring changes in cellular types as related to disease state over time.

Generally, the method of the invention comprises the following steps. An infrared beam is directed to the sample through an Attenuated Total Reflection (ATR) microscope objective of a microscope. Significantly, the depth of penetration of the infrared light in the sample is controlled to avoid interference resulting from the absorptive substrate supporting the sample. Infrared light reflected from the sample is collected and analyzed. The resulting infrared spectrum can be used to identify different cellular types such as benign, hyperplastic, or malignant, or the presence or absence of such cellular anomalies.

The sample can also be scanned under the microscope using visible light to identify sites of interest for infrared measurements. Alternatively, the sample can be mapped by infrared ATR microspectroscopy under automated control at different detection sites without the need for previous visual inspection to identify sites of interest.

It is a feature of the present invention to perform infrared ATR microspectroscopic measurements on a biological sample supported on an infrared-absorptive substrate such as a plain glass slide. As a result, a sample on a glass slide can be used for both pathologic and infrared studies. No special sample preparation is required for the infrared study.

Other objects and advantages will become apparent with reference to the following detailed description when taken in conjunction with the drawings.

BRIEF DESCRIPTION OF THE DRAWINGS

FIG. 1 is a schematic top view of a biological sample that may be studied using the method of the invention;

FIG. 2 is a schematic diagram showing a Fourier Transform Infrared (FTIR) microscope system for performing the method of the invention;

FIG. 3 is a schematic diagram showing a biological sample supported on a glass slide and positioned under an Attenuated Total Reflection (ATR) objective for infrared study; and FIG. 4 shows infrared spectra of benign, hyperplastic, and malignant cells in breast tissue samples supported on glass slides collected by infrared ATR microspectroscopy.

While the invention is susceptible of various modifications and alternative constructions, certain illustrated embodiments have been shown in the drawings and will be described below. It should be understood, however, that there is no intention to limit the invention to the specific forms disclosed, but, on the contrary, the invention is to cover all modifications, alternative constructions and equivalents falling within the spirit and scope of the invention as defined by the appended claims.

DETAILED DESCRIPTION OF THE PREFERRED EMBODIMENT

Turning now to the drawings, FIG. 1 shows, in schematic form, a biological sample 10 which can be studied by the method of the invention. The sample 10 is in the form of a layer supported on a substrate that is absorptive in the energy range typically used for infrared studies. The biological sample 10 contains cells of different cellular types which can be identified using the method of the invention. For instance, the sample 10 may contain benign, hyperplastic, and malignant cells at different sites 14, 16, 18, respectively.

In the illustrated embodiment, the infrared-absorptive substrate supporting the sample 10 is a plain glass slide 12 of the type commonly used to prepare samples for standard pathologic studies. Such a glass slide typically exhibits strong absorption in the typical infrared energy range of interest for studying the biological sample. Significantly, if the spectral response from the sample cannot be separated from the spectral response from the glass, absorption features of the sample in the measured spectrum will be masked by those of the glass. Glass also does not provide a good reflective surface for infrared light. For these reasons, a biological sample supported on such a glass slide cannot be studied by conventional infrared spectroscopic techniques and is typically considered unsuitable for infrared studies.

Generally, the method of the invention is based on Fourier Transform Infrared (FTIR) Attenuated Total Reflection (ATR) microspectroscopy. FIG. 2 shows a system for implementing the method of the invention. As shown in FIG. 2, the system includes a microscope 20 which can be used for both visual inspection of the sample and for measuring infrared spectra from the sample. The microscope has an object stage 22 on which the sample to be studied is mounted. The stage can be moved manually or under automated control. A video camera 24 is connected to the microscope for taking pictures of the sample.

Instrumentation and apparatus for performing FTIR and ATR measurements are available from a number of commercial suppliers, including Nicolet Instruments Corp., Perkin-Elmer, Bruker Instruments, Inc., Bio-Rad Digilab Division, Spectra-Tech, Inc., and others. ATR microanalysis can be further performed using accessories such as the SplitPea from Harrick Scientific Corp., or with imaging capabilities using accessories such as the InspectIR from Spectra-Tech, Inc.

The microscope 20 is connected to an FTIR spectrometer 25 that includes an infrared source 26 for providing mid-infrared energy suitable for infrared spectroscopic studies. The infrared attenuated total reflection from the sample 10 is collected by the microscope and detected by a detector 28. The signals from the detector 28 are coupled to a data analyzer 30 which analyzes the infrared intensity and energy to identify the existence of different cellular types in the sample. The data analyzer 30 may include a computer system or data processing system properly programmed and having components for interfacing with other components of the microscope. Alternatively, the spectrometer components, such as the infrared source and the beam splitter, can be built into the microscope as a single system.

In accordance with a feature of the invention, an Attenuated Total Reflection (ATR) microscope objective 32 is used to interface with the sample for measuring infrared spectral response of the sample. In the illustrated embodiment, the ATR microscope objective 32 is a slide-on device which is moved out of the optical path when the sample is visually inspected under the microscope and slid in the optical path for taking infrared measurements. The interface between the sample and the ATR microscope objective during an infrared reflection measurement is shown in FIG. 3. The ATR microscope objective 32 includes an ATR crystal 34 which has a higher index of refraction for infrared light than the sample 10. Typically, the ATR crystal is made from Si, Ge, or ZnSe.

To measure infrared spectral response from the sample 10, the ATR crystal 34 is brought into contact with the sample surface. An infrared beam 36 is then directed to the sample through the ATR crystal 34 at a pre-selected angle which is greater than a critical angle so that total internal reflection occurs at the interface 38 of the crystal and the sample. The electromagnetic field of the infrared beam, however, does not terminate abruptly at the crystal surface but extends into the sample for a short distance. The strength of the electromagnetic field in the sample decreases rapidly (exponentially) with the distance from the sample/crystal interface 38. The electromagnetic field in the sample is absorbed by the sample at energies where the sample material is absorptive. The reflected infrared light 40 from the sample 10 thus carries information of the absorption characteristics of the sample. The reflected infrared light 40 passes through the ATR crystal 34 and is collected by the microscope 20, detected by the detector 28, and analyzed by the analyzer 30.

In accordance with the invention, the problem of spectral contamination by the absorption of the glass slide 12 is avoided by controlling the penetration depth of the infrared light in the sample to minimize the amount of infrared light reaching the glass substrate, thereby avoiding contribution of the glass substrate in the measured infrared spectrum. The penetration depth can be controlled by selecting the energy range of the incident infrared beam 36. Generally, the penetration depth decreases with shorter wavelengths. A shorter penetration depth is thus obtained by selecting a higher energy range of the incident infrared beam. For mid-infrared, the penetration depth is typically on the order of 0.5 to 3.5 microns. Biological samples typically have a thickness on the order of 5 microns and are therefore suitable for study by ATR microspectroscopy.

Alternatively, if the energy range of the incident infrared beam is already selected so that the penetration depth is fixed, the infrared light can be prevented from reaching the glass slide 12 by adjusting the contact pressure between the ATR crystal 34 and the sample 10, which has the effect of moving the interface 38 between the ATR crystal and the sample further away from or closer to the glass substrate. The sample has to be at least as thick as the penetration depth to avoid infrared light reflection by the glass slide 12. In the embodiment of FIG. 1, a contact pressure monitor 29 is used to monitor the contact pressure. The contact pressure monitor 29 permits the contact conditions to be reproducible and excessive contact pressure to be avoided.

In one mode of the invention, a sample under study is first inspected under the microscope 20 using visible light to identify one or more sites of interest. For example, the sample 10 of FIG. 1 may be visually scanned, and the sites 14, 16, and 18 may be determined to be of interest based on their locations, structures, or other visual appearances. During the visual inspection, the ATR microscope objective 32 is positioned out of the path of the visible light between the microscope and the sample. After the sites of interest have been visually identified, the ATR microscope objective 32 is moved to its operation position in the light path. The ATR crystal 34 is then brought into contact with the sample, and the contact pressure is set and monitored. An infrared beam is directed to the sample through the ATR crystal, and the attenuated total reflection from the sample passes through the ATR element and is collected and analyzed.

In an alternative mode of operation, the sample is mapped by ATR infrared microspectroscopy at selected detection sites under automated control without utilizing prior visual inspection to identify sites of interest. In this embodiment, the object stage 22, on which the sample 10 on the glass slide 12 is mounted, is moved under the automated control of a scan controller 23, which may be a computer or other processor operatively coupled to the microscope. After the ATR infrared measurement is performed on one detection site in the sample, the object stage 22 is moved under the control of the scan controller so that the next detection site is positioned for ATR infrared measurement. This process is repeated until all detection sites are measured. The infrared spectrum from each of the detection sites is analyzed to determine the cellular types or presence of anomalies at that site. The positions of the detection sites may be selected in different ways. For instance, the detection sites may be spaced by constant intervals. More complicated patterns or even randomized selections of the detection sites can, of course, be used.

The method of the invention can be advantageously used to study different types of biological samples supported on plain glass slides. Samples may include, but are not limited to, tissue specimens taken from a variety of organs, such as breast, prostate, bladder, colon, cervix, skin, etc. Samples may also comprise exfoliated cells supported on the glass slide. A sample comprising exfoliated cells may be, for example, a Papanicolau smear, a cervical specimen, an endocervical specimen, an ectocervical specimen, a vaginal specimen, or a uterus specimen, etc. Samples may also comprise blood cells. The sample may be prepared in a manner standard for pathologic studies.

Significantly, the sample may be an archival sample prepared years earlier. An archival tissue sample is typically a fixed microtomed thin layer on a plain glass slide. With such a sample, the sample preparation for the infrared study may require only the removal of a cover slip.

The tissue sample may be initially covered with paraffin. In this case, the sample is deparaffinized before being studied by the method of the invention. The deparaffinized tissue sample is preferably stained with a suitable dye, such as Haematoxylin-Eosin (H&E), to allow easy visual identification of different cell structures under a microscope. The staining, however, is not necessary for the ATR infrared study.

Thus, the method of the invention is useful for diagnosing and monitoring disease states for biological samples. The method is particularly useful for detecting and monitoring cancerous conditions in such samples.

By way of example, FIG. 4 shows three infrared spectra 42, 44, 46 of different cellular types taken from breast tissue samples containing benign cells, hyperplastic cells, and infiltrating ductal carcinoma cells. The infrared spectra were measured on a Nicolet 750 FTIR spectrometer (Nicolet Instruments Corp., Madison, Wis.) connected to a Nic-Plan microscope (Nicolet Instruments) equipped with a liquid nitrogen cooled HgCdTe detector. Absorbance was measured in the mid-infrared range and plotted over the range of 1800 $cm^{-1}$ to about 1100 $cm^{-1}$.

An ATR slide-on accessory (Spectra-Tech, Inc., Shelton, Conn.) with a Si ATR crystal was mounted on a 15X Reflachromat™ Cassegrain objective. The slide-on ATR accessory has one position for viewing the sample and another position for infrared measurements. The ATR slide-on accessory is attached to a Contact Alert System (Spectra-Tech, Inc.) to indicate when the contact between the sample and the ATR crystal is made and to monitor the contact pressure. For infrared measurements, a fixed round upper aperture with a diameter of 1.5 mm was used to reduce the sampling area from which the infrared reflection is measured. The resulting sampling area is about 29 microns.

Seven breast tissue samples from the same biopsy specimen were mounted on plain glass slides of the type used for conventional pathologic studies and were initially paraffin-embedded. The estimated average thickness of the tissue samples was about 5 microns. Before taking infrared microspectroscopic measurements, the samples were deparaffinized and then stained with haematoxylin-eosin (H&E) according to standard histology procedure. The completeness of the deparaffinization was confirmed by the lack of paraffin-induced features in the infrared spectra. A conventional pathologic inspection was performed on the samples, and sites containing benign, hyperplasia, and malignant cells were identified. The spectrum 42 is an average of twenty-six spectra taken at common sites of benign cells for the seven sample slides. The spectrum 44 is an average of twenty-five spectra taken at common sites of hyperplasia cells for the seven slides. The spectrum 46 is an average of twenty-five spectra taken at common sites of malignant cells for the seven slides. A background spectrum collected by taking a spectrum of the bare ATR crystal (i.e., without contact with a sample) has been subtracted from these spectra. The spectra have also been normalized to a maximum absorption of 1.0 at about 1650 $cm^{-1}$.

Although the three spectra have apparent similarities, significant differences are observed. The largest differences distinguishing the spectrum of benign cells from the spectra of malignant and hyperplasia cells include a shoulder at about 1205 cm$^{-1}$, a shoulder at about 1283 cm$^{-1}$, the absence of a peak at 1304 cm$^{-1}$, a peak at 1340 cm$^{-1}$, the difference of peak shape around 1388 cm$^{-1}$, the difference in intensity of the shoulders at 1515 cm$^{-1}$ and 1550 cm$^{-1}$, and some frequency shift of a peak around 1645 cm$^{-1}$.

Different methods can be used to analyze the data of infrared ATR microspectroscopy measurements and identify the cellular types in a biological sample. For instance, a visual comparison of the spectrum of a site of interest with a reference spectrum of benign cells or other reference spectra of different cellular types may be sufficient for determining the types of cells at that site of interest. Alternatively, the reference spectrum for benign cells can be subtracted from the spectrum of the site of interest to emphasize the differences. More sophisticated statistical analyses can also be used to assist in the identification of cellular types. For instance, several multivariate classification methods, including partial-least square (PLS), partial component regression (PCR), and linear discriminant analysis (LDA) have been shown to provide satisfactory results. Among these multivariate methods, the LDA method is preferred because it provides the best results and is simple to use.

It can be appreciated from the foregoing detailed discussion that the invention provides a method for performing an infrared study on a biological sample mounted on an infrared-absorptive substrate, such as a plain glass slide of a type commonly used in a pathology laboratory. The method is non-destructive so that the same sample can be used for both infrared and standard pathologic studies. No special sample preparation is required for the infrared study beyond that already used in pathologic studies. This method allows infrared measurements to be performed on a large amount of archival samples that cannot be studied with conventional infrared spectroscopic techniques. Thus, the method allows application of infrared spectroscopy to more biological samples than has been available in the past.

What is claimed is:

1. A method of identifying cellular types in a biological sample supported on an infrared-absorptive substrate, the method comprising the steps of:

directing an infrared beam to the biological sample through an attenuated total reflection (ATR) objective at a penetration depth of the biological sample controlled to avoid spectral response from the substrate;

detecting infrared light reflected by the biological sample; and analyzing the infrared light reflected by the biological sample to identify cellular types in the biological sample.

2. A method as in claim 1, wherein the infrared-absorptive substrate is a glass slide.

3. A method as in claim 2, wherein an energy range of the infrared beam is within about 400 cm$^{-1}$ to 4000 cm$^{-1}$.

4. A method as in claim 1, wherein the cellular types are cancerous cells.

5. A method as in claim 1, wherein the ATR objective is in contact with the biological sample.

6. A method as in claim 5, wherein the detecting step includes collecting the infrared light reflected by the sample through the ATR objective.

7. A method as in claim 1, wherein the biological sample is a tissue sample.

8. A method as in claim 7, further including the step of deparaffinizing the tissue sample before directing the infrared beam to the sample.

9. A method as in claim 1, wherein the biological sample is an archival sample.

10. A method as in claim 1, wherein the biological sample is a blood sample.

11. A method as in claim 1, wherein the sample includes exfoliated cells.

12. A method as in claim 11, wherein the biological sample is selected from the group of a Papanicolaou smear, a cervical specimen, an ectocervical specimen, an endocervical specimen, a vaginal specimen, and a uterus specimen.

13. A method of identifying cellular types in a biological sample supported on an infrared-absorptive substrate, comprising the steps of:

inspecting the sample with a microscope using visible light to identify a site of interest in the sample;

directing an infrared beam at the site of interest through an ATR microscope objective at a penetrating depth in the biological sample controlled to avoid spectral response by the infrared-absorptive substrate;

detecting infrared light reflected by the biological sample;

analyzing the detected infrared light reflected by the biological sample to identify cellular types at the site of interest.

14. A method as in claim 13, wherein the infrared-absorptive substrate is a glass slide.

15. A method as in claim 13, wherein the cellular types are cancerous cells.

16. A method as in claim 13, wherein the inspecting step includes identifying cellular types at the site of interest based on visual appearance of the site of interest.

17. A method as in claim 13, wherein the biological sample is a tissue sample.

18. A method as in claim 13, wherein the biological sample includes exfoliated cells.

19. A method as in claim 13, wherein the biological sample is an archival sample.

20. A method of identifying cellular types in a biological sample supported on an infrared-absorptive substrate, comprising the steps of:

mounting the sample on an object stage of a microscope;

selecting a plurality of detection sites in the biological sample;

for each detection site, moving, under automated control, the object stage to position said each detection site for study by the microscope;

directing an infrared beam at said each detection site in the sample through an ATR microscope objective at a penetrating depth in the biological sample controlled to avoid spectral response by the infrared-absorptive substrate;

detecting infrared light reflected from said each detection site; and analyzing the detected infrared light reflected from said each detection site to identify cellular types at said each detection site.

21. A method as in claim 20, wherein the infrared-absorptive-substrate is a glass slide.

22. A method as in claim 20, wherein the cellular types are cancerous cells.

23. A method as in claim 20, wherein the biological sample is a tissue sample.

24. A method as in claim 20, wherein the biological sample includes exfoliated cells.

* * * * *